(12) United States Patent
Fedurco

(10) Patent No.: US 9,126,907 B2
(45) Date of Patent: Sep. 8, 2015

(54) SULPHUR-CONTAINING AND SULPHONATED AROMATIC PERFLUOROALKANE MONOMER

(75) Inventor: Milan Fedurco, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 33 days.

(21) Appl. No.: 13/812,892

(22) PCT Filed: Jul. 6, 2011

(86) PCT No.: PCT/EP2011/061427
§ 371 (c)(1),
(2), (4) Date: Mar. 25, 2013

(87) PCT Pub. No.: WO2012/016779
PCT Pub. Date: Feb. 9, 2012

(65) Prior Publication Data
US 2013/0197110 A1    Aug. 1, 2013

(30) Foreign Application Priority Data
Aug. 4, 2010  (FR) .................... 10 56439

(51) Int. Cl.
C07C 317/14    (2006.01)
C07C 323/66    (2006.01)
(Continued)

(52) U.S. Cl.
CPC .......... *C07C 317/14* (2013.01); *B01J 49/0047* (2013.01); *C07C 323/66* (2013.01);
(Continued)

(58) Field of Classification Search
USPC ............................................ 521/27; 528/391
See application file for complete search history.

(56) References Cited

U.S. PATENT DOCUMENTS

| | | | |
|---|---|---|---|
| 6,495,209 B1 | 12/2002 | Cisar | 427/384 |
| 7,037,614 B1 * | 5/2006 | Cooray et al. | 429/494 |
| 7,901,821 B2 | 3/2011 | Buchi et al. | 429/429 |
| 2004/0236062 A1 * | 11/2004 | Hofmann | 528/125 |

(Continued)

FOREIGN PATENT DOCUMENTS

| | | |
|---|---|---|
| JP | 2001-277720 A | 10/2001 |
| WO | WO 2005/006472 A1 | 1/2005 |

(Continued)

OTHER PUBLICATIONS

A.E. Feiring et al., "Fluorinated Poly(ether Sulfone)s," Journal of Polymer Science: Part A: Polymer Chemistry, vol. 28 (1990), pp. 2809-2819.*

(Continued)

*Primary Examiner* — Peter D Mulcahy
*Assistant Examiner* — Henry Hu
(74) *Attorney, Agent, or Firm* — Fitzpatrick, Cella, Harper & Scinto

(57) ABSTRACT

A sulphur-containing and sulphonated aromatic perfluoroalkane monomer is provided that can be used for the manufacture of a polymer membrane for a PEM-type fuel cell. The perfluoroalkane monomer is a functionalized polymer that has a structure corresponding to a formula (I):

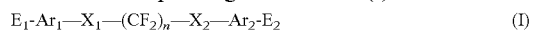

Figure 1A:
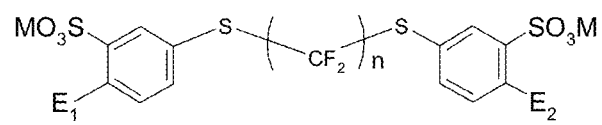

in which:
  n is in a range from 1 to 20;
  $X_1$ and $X_2$, which are identical or different, represent S, SO, or $SO_2$;
  $Ar_1$, $Ar_2$, which are identical or different, represent a phenylene group, at least one of $Ar_1$ and $Ar_2$ bearing a sulphonic ($-SO_3H$) group or a sulphonate ($-SO_3M$) group, in which M represents an alkali metal cation; and
  $E_1$ and $E_2$, which are identical or different, represent an electrophilic group such as a halogen, specifically fluorine or chlorine.

14 Claims, 14 Drawing Sheets

(I-3)

(51) Int. Cl.
*H01M 8/10* (2006.01)
*C08G 75/20* (2006.01)
*B01J 49/00* (2006.01)

(52) U.S. Cl.
CPC ............ *C08G 75/20* (2013.01); *H01M 8/1025* (2013.01); *H01M 8/1027* (2013.01); *H01M 8/1032* (2013.01); *H01M 8/1039* (2013.01); *H01M 8/1088* (2013.01); *Y02E 60/521* (2013.01)

(56) References Cited

U.S. PATENT DOCUMENTS

| | | | |
|---|---|---|---|
| 2005/0221135 A1* | 10/2005 | Cooray et al. | 429/20 |
| 2008/0160363 A1 | 7/2008 | Tsukada | 429/19 |
| 2010/0040930 A1 | 2/2010 | Delfino et al. | 429/34 |
| 2010/0173227 A1 | 7/2010 | Olsommer | 429/514 |
| 2011/0311899 A1* | 12/2011 | Onodera et al. | 429/482 |

FOREIGN PATENT DOCUMENTS

| | | |
|---|---|---|
| WO | WO 2006/012953 A2 | 2/2006 |
| WO | WO 2006/012954 A1 | 2/2006 |
| WO | WO 2006/100029 A1 | 9/2006 |
| WO | WO 2008/125174 A1 | 10/2008 |
| WO | 2012/016780 A1 | 2/2012 |
| WO | WO-2012/016779 A1 * | 2/2012 |

OTHER PUBLICATIONS

D.M. Tigelaar et al., "Synthesis and Properties of Novel Proton-Conducting Aromatic Poly(ether sulfone)s That Contain Triazine Groups," Macromolecules, vol. 42, pp. 1888-1896 (2009).

R. Souzy et al., "Functional fluoropolymers for fuel cell membranes," Progress in Polymer Science, vol. 30 (2005), pp. 644-687.

R.D. Spencer et al., "Determination of Four Closely Related Triaryl-s-Triazines by Infrared Spectrometry," Analytical Chemistry, vol. 35, No. 11 (Oct. 1963), pp. 1633-1636.

X. Zhu et al., "Challenging reinforced composite polymer electrolyte membranes based on disulfonated poly(arylene ether sulfone)-impregnated expanded PTFE for fuel cell applications," Journal of Material Chemistry, vol. 17 (2007), pp. 386-397.

L.V. Johnson, et al., "Organic Fluorides. Part XIV. The Synthesis of Some Aromatic Fluoro-and Chloro-compounds", J. Chem. Soc., pp. 4710-4713 (1952).

* cited by examiner (I-1)

(I-2)

(I-3)

(II-1)

(II-2)

(II-3)

(III-1)

(III-2)

(III-3)

Fig. 7
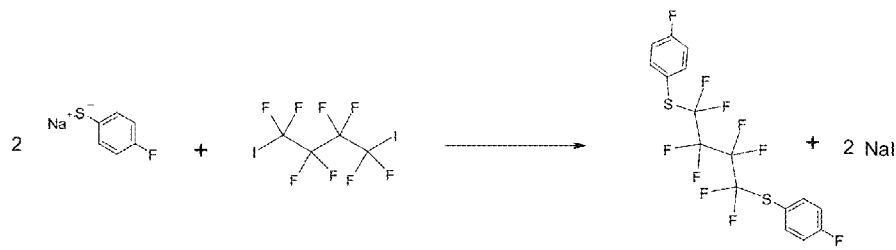
Compound 1
Fig. 7A
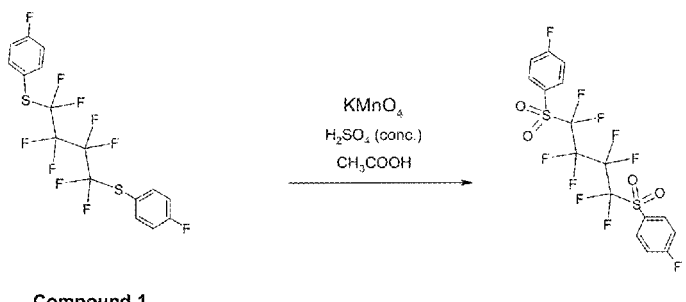
Compound 1 → Compound 2
Fig. 7B
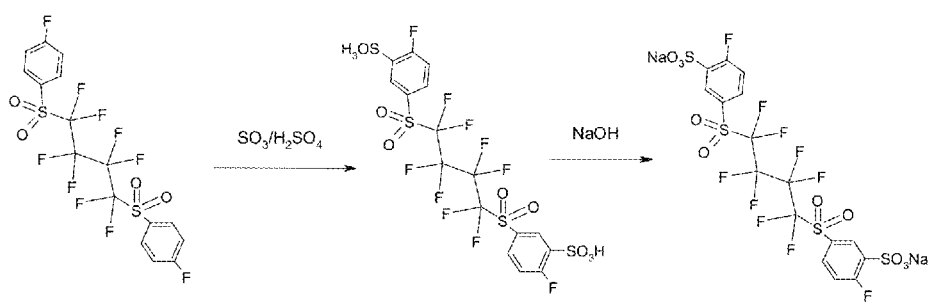
Compound 2 → Compound 3
Fig. 7C

Fig. 9
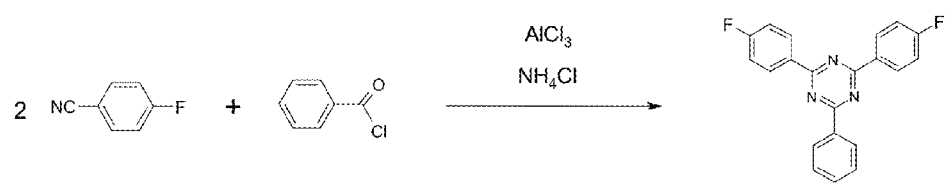
Compound 4
*Fig. 9A*
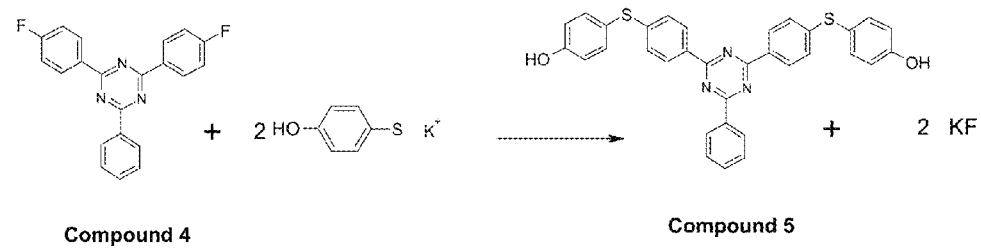
Compound 4          Compound 5
*Fig. 9B*
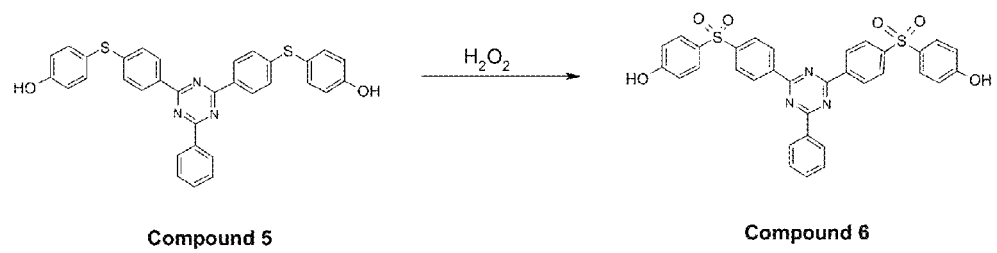
Compound 5          Compound 6
*Fig. 9C*

Polymer 1

Fig. 13
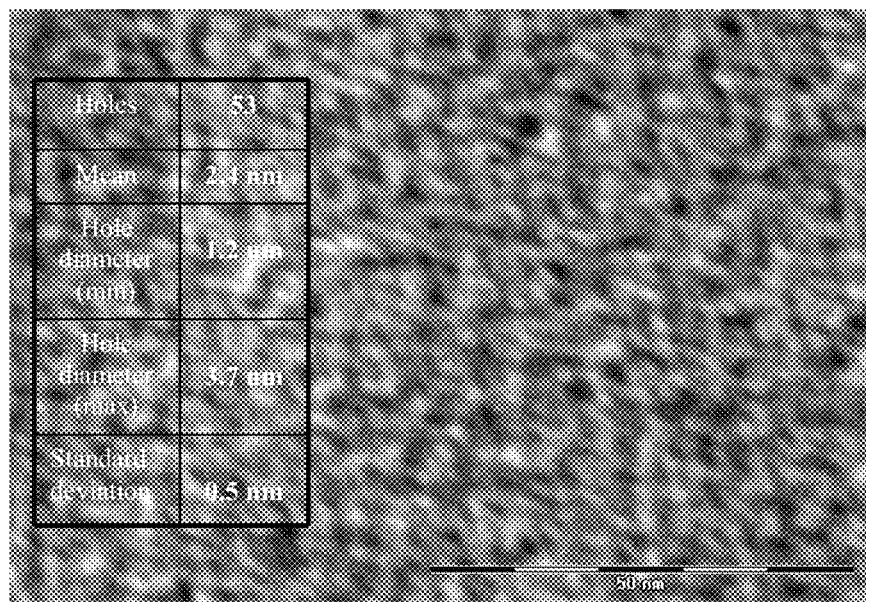
Fig. 13A
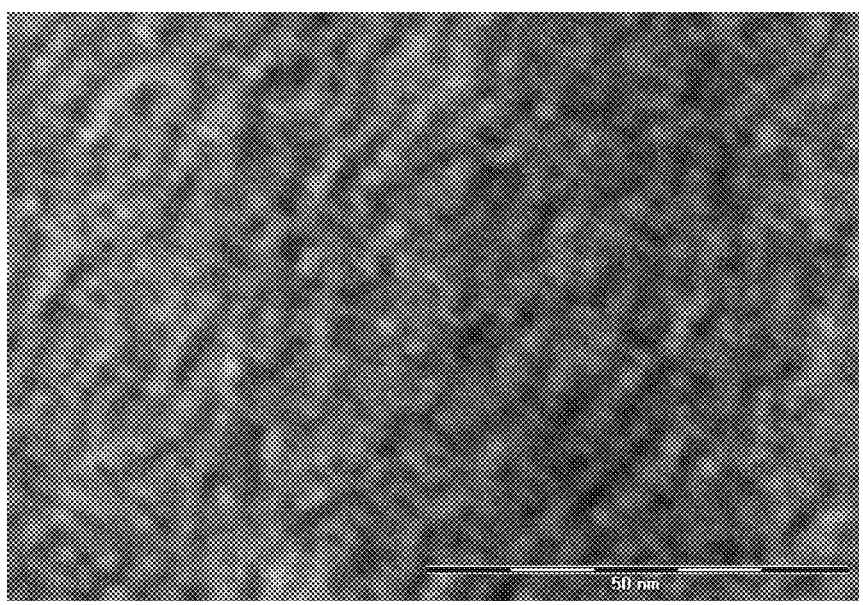
Fig. 13B

SULPHUR-CONTAINING AND SULPHONATED AROMATIC PERFLUOROALKANE MONOMER

I. FIELD OF THE INVENTION

The present invention relates to the monomers which can be used for the synthesis of polymers intended in particular, in the sulphonated form, to constitute a solid electrolyte or membrane in a fuel cell.

It relates more particularly to the above monomers of the aromatic type comprising a central structural unit of the perfluoroalkylene type.

II. STATE OF THE ART

The recent interest in fuel cells arises from their ability to convert chemical energy into electricity with a relatively high yield and a low emission of environmental pollutants. The use of such electrochemical devices extends today from the motor vehicle industry to portable computers, to mobile phones, to the stationary generation of electrical energy and to other applications comprising exploration of the sea and space.

It should be remembered first of all that a fuel cell is an electrochemical energy generator in which a chemical reaction between hydrogen and oxygen is maintained under control, which reaction will produce water (reverse reaction to electrolysis). It produces electrical energy and heat. The electrolyte therein is typically composed of a PEM (Polymer Electrolyte Membrane) which conducts protons and which is capable of separating the reactive entities, consisting of two very distinct nanophases: on the one hand, a hydrophobic part which provides mechanical integrity, watertightness and gastightness (the gases being $H_2$ and $O_2$) and, on the other hand, a sulphonated part consisting of narrow hydrophilic channels allowing the protons to pass and thus providing the ionic conductivity of the cell. This polymer membrane is positioned between the anode and the cathode of the cell, such an assembly being commonly referred to as "MEA" (Membrane Electrode Assembly).

Such fuel cells, MEA assemblies and their general operating principles are well known. They have been described in a very large number of documents; mention may be made, as examples, of the general article entitled "*Functional fluoropolymers for fuel cell membranes*" by Renaud Souzy & Bruno Ameduri, Prog. Polymer Sci., 30 (2005), 644-687, and Patent Applications WO 2005/006472, WO 2006/012953, WO 2006/012954, WO 2006/100029 and WO 2008/125174.

A polymeric material which is a good candidate for a PEM fuel cell must meet very high requirements as regards its mechanical, physical and chemical properties. Ideally, the MEA assembly is expected to be able to operate for thousands of hours at relatively high temperatures (60 to 100° C. in the case of PEM cells, up to 160° C. in the case of methanol cells referred to as DMFCs) while being exposed to particularly high humidity and acidic pH values close to zero. The majority of known polymers undergo decomposition under such conditions, whether of aliphatic type or of aromatic type.

Aliphatic copolymers derived from perfluorosulphonic acid, sold, for example, under the Nafion® or Flemion® name, have been intensively employed as conducting membranes in fuel cells of the hydrogen/air, hydrogen/oxygen or methanol/air type.

Despite a very good ion conductivity and a high chemical stability, the use of polymers of the Nafion® type is first of all not suited to employment in fuel cells of the methanol type, due to reduced performance for the highest operating temperatures, due to a significant increase in permeability of the membrane with regard to the methanol.

Another known disadvantage of the polymers of the Nafion® type, in operation in the cell, is their relatively limited chemical stability. This is because perfluoropolymers are known to absorb large amounts of water responsible for repeated dimensional changes and swellings of the membrane: repeated cycles of drying and humidification, during successive shutdowns and startups of the fuel cell, result in an increased permeability to gases ($H_2$ and $O_2$); this increased permeability is responsible for the formation of hydrogen peroxide and free radicals (OH), so many mechanisms which can result in rapid degradation in a membrane and in the premature end of life of the fuel cell. In order to limit these dimensional changes and to thus improve the endurance of the membranes, it has been proposed in particular to add, as reinforcing polymer, a second fluoropolymer, in particular a PTFE (polytetrafluoroethylene) of the expanded microporous (or "ePTFE") type, and to thus form tougher composite membranes (see, for example, U.S. Pat. No. 6,495,209).

Finally, another major disadvantage of the polymers of the Nafion® type is the cost of their synthesis, without mentioning a base chemistry which no longer corresponds today to the most recent requirements in terms of the environment and of health and safety regulations.

Consequently, much research has been carried out in the past in an attempt to reduce the cost of the PEM membranes.

It has in particular been proposed to replace the above aliphatic polymers with aromatic polymers, which are lower in cost and which furthermore have the advantage of exhibiting a reduced permeability to the gases ($H_2$ and $O_2$).

Examples of such polymers are, for example, poly(arylene-ether-sulphone)s, sold in particular under the "Udel" or "Radel" names, or poly(ether-ether-ketone)s, sold, for example, under the "PEEK" name. The above aromatic polymers, once sulphonated, still do not make it possible today to achieve the compromise in performance and in cost offered with the fluorinated aliphatic polymers of the Nafion® type. In addition, these aromatic polymers generally mix poorly with an ePTFE-type polymer and the membranes which result therefrom thus cannot be easily reinforced with an ePTFE polymer, such a reinforcing requiring a preliminary surface treatment of the ePTFE polymer by plasma or by the chemical route in very aggressive chemical media (see, for example, the paper entitled "*Challenging reinforced composite polymer electrolyte membranes based on disulfonated poly(arylene-ether-sulfone)-impregnated expanded PTFE for fuel cell applications*", Xiaobing Zhu et al., J. Mat. Chem., 2007, 386-397).

Other examples of polymers of the aromatic type have been described more recently in the patent documents US2005/0221135 and U.S. Pat. No. 7,037,614. They are sulphonated triazine polymers, the monomers of which are connected via ether (—O—) bridges. The syntheses described in these documents are complex, expensive and difficult to reproduce. In addition, it has been found that their chemical and dimensional stability is insufficient even after a final crosslinking treatment of the membranes, which treatment furthermore requires another complex and expensive chemistry.

III. BRIEF DESCRIPTION OF THE INVENTION

During their research studies, the Applicant Companies have found a novel aromatic monomer, more precisely a specific aromatic perfluoroalkane monomer, which can be used for the synthesis of a polymer membrane making it possible to overcome, at least in part, the abovementioned disadvantages.

This aromatic perfluoroalkane monomer of the invention corresponds to the formula (I):

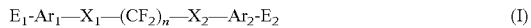

$$E_1-Ar_1-X_1-(CF_2)_n-X_2-Ar_2-E_2 \qquad (I)$$

in which:

n is in a range from 1 to 20;

the symbols $X_1$ and $X_2$, which are identical or different, represent S, SO or $SO_2$;

the symbols $Ar_1$ and $Ar_2$, which are identical or different, represent a phenylene group, at least one of which bears a sulphonic group —$SO_3H$ or a sulphonate group —$SO_3M$, M representing an alkali metal cation;

the symbols $E_1$ and $E_2$, which are identical or different, represent an electrophilic functional group (i.e., an electron-withdrawing group).

Starting from this monomer in accordance with the invention, it has proven possible to synthesize a polymer which, in comparison with the polymers of the prior art described above, has a markedly improved chemical stability and a markedly improved resistance to oxidation. It makes it possible to manufacture PEM membranes which, unexpectedly, in comparison with commercial membranes of the Nafion® type developed a long time ago, exhibit an equivalent chemical and dimensional stability and an equivalent ion conductivity. Finally, the polymer resulting from the monomer of the invention can, which is not the least of its advantages, be rendered compatible with a microporous ePTFE polymer for optimal reinforcing of the membrane, without requiring the surface treatments which were mentioned above.

The invention also relates to a process for the synthesis of a polymer by polycondensation of at least one aromatic perfluoroalkane monomer in accordance with the invention.

The invention also relates to the use of an aromatic perfluoroalkane monomer in accordance with the invention for the manufacture of a polymer membrane which can be used in a fuel cell of the PEM type.

Figure 1B:
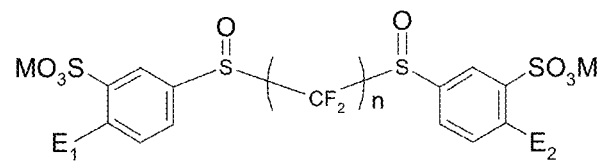
Figure 1C:
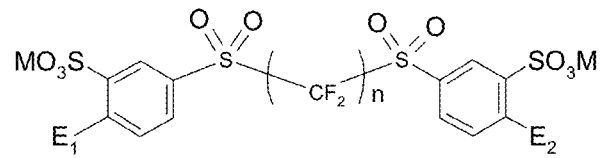
Figure 2A:
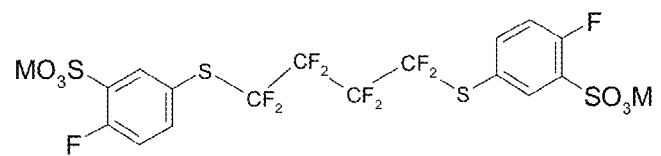
Figure 2B:
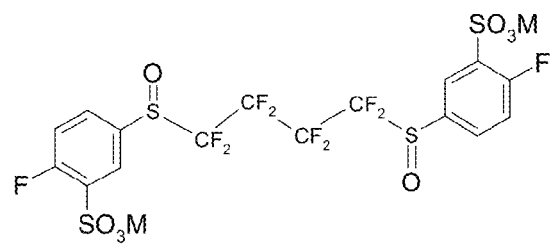
Figure 2C:
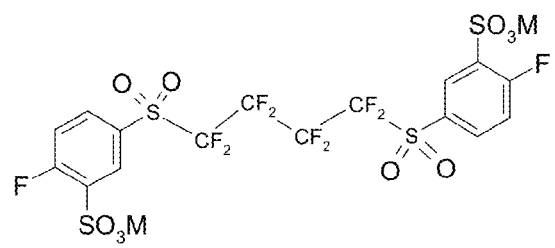
Figure 3A:
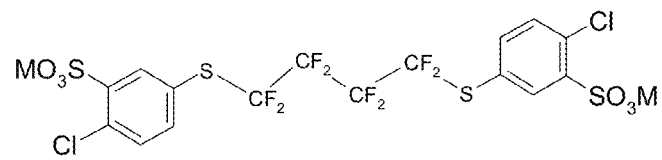
Figure 3B:
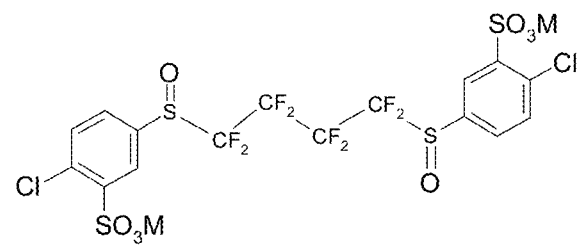
Figure 3C:
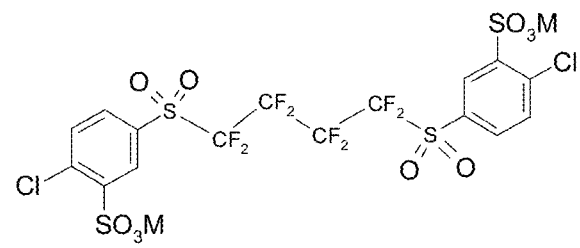
Figure 4:
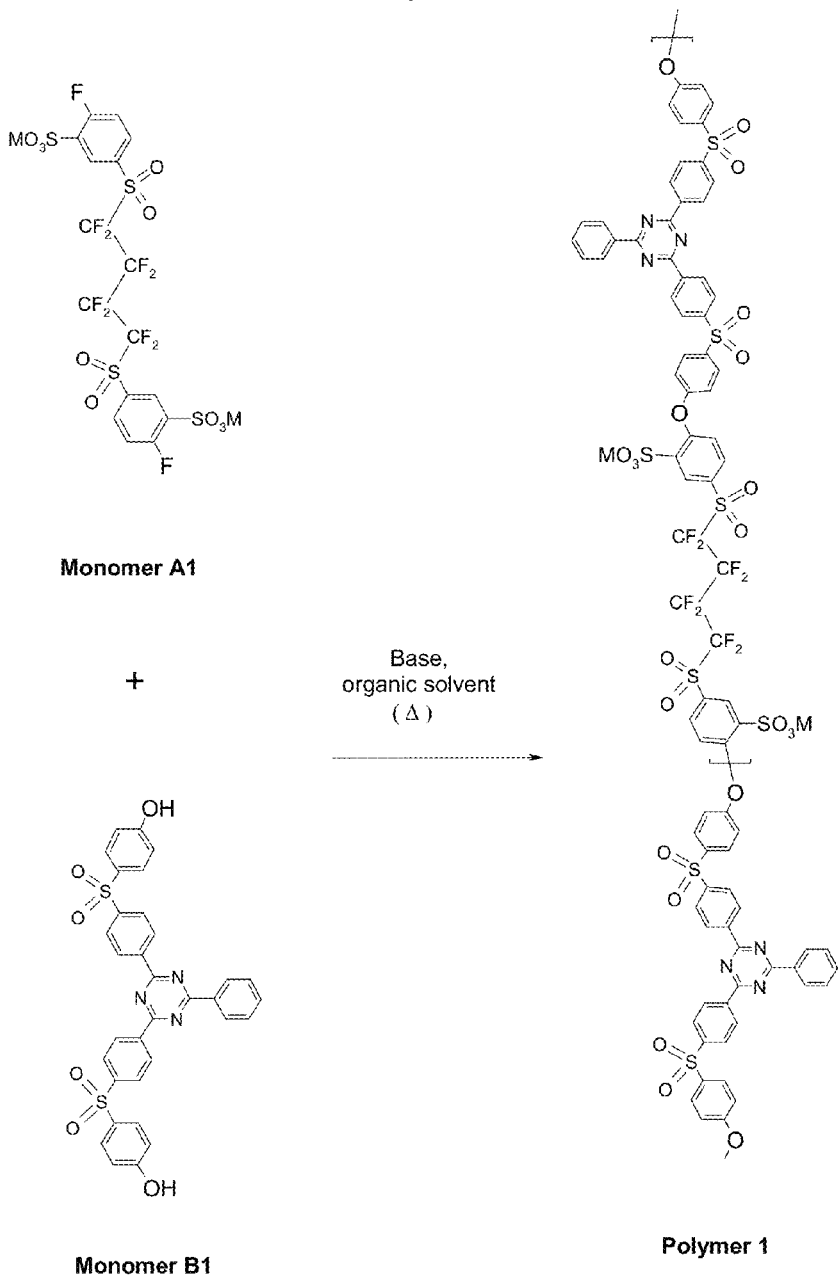
Figure 5:
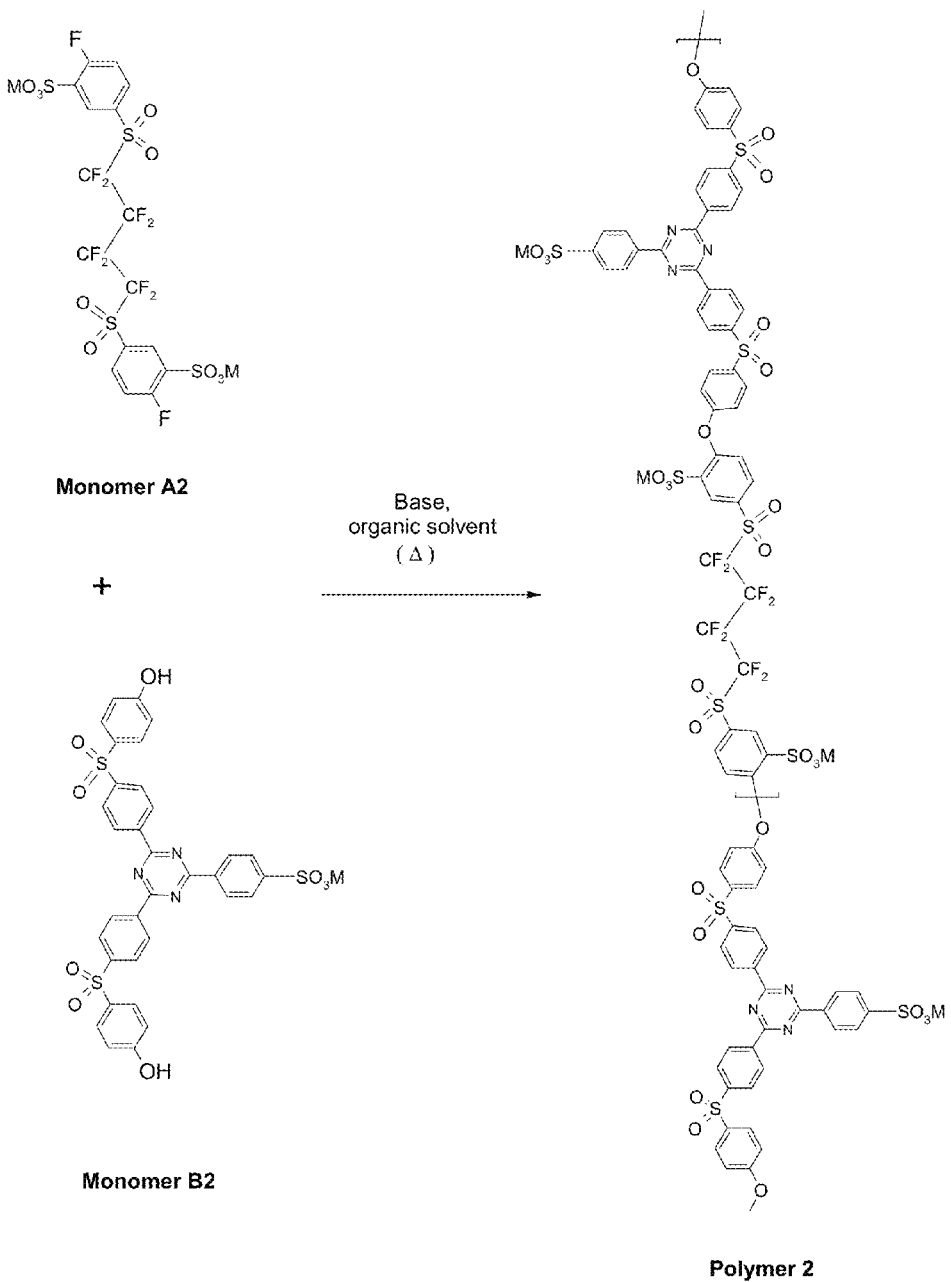
Figure 6:
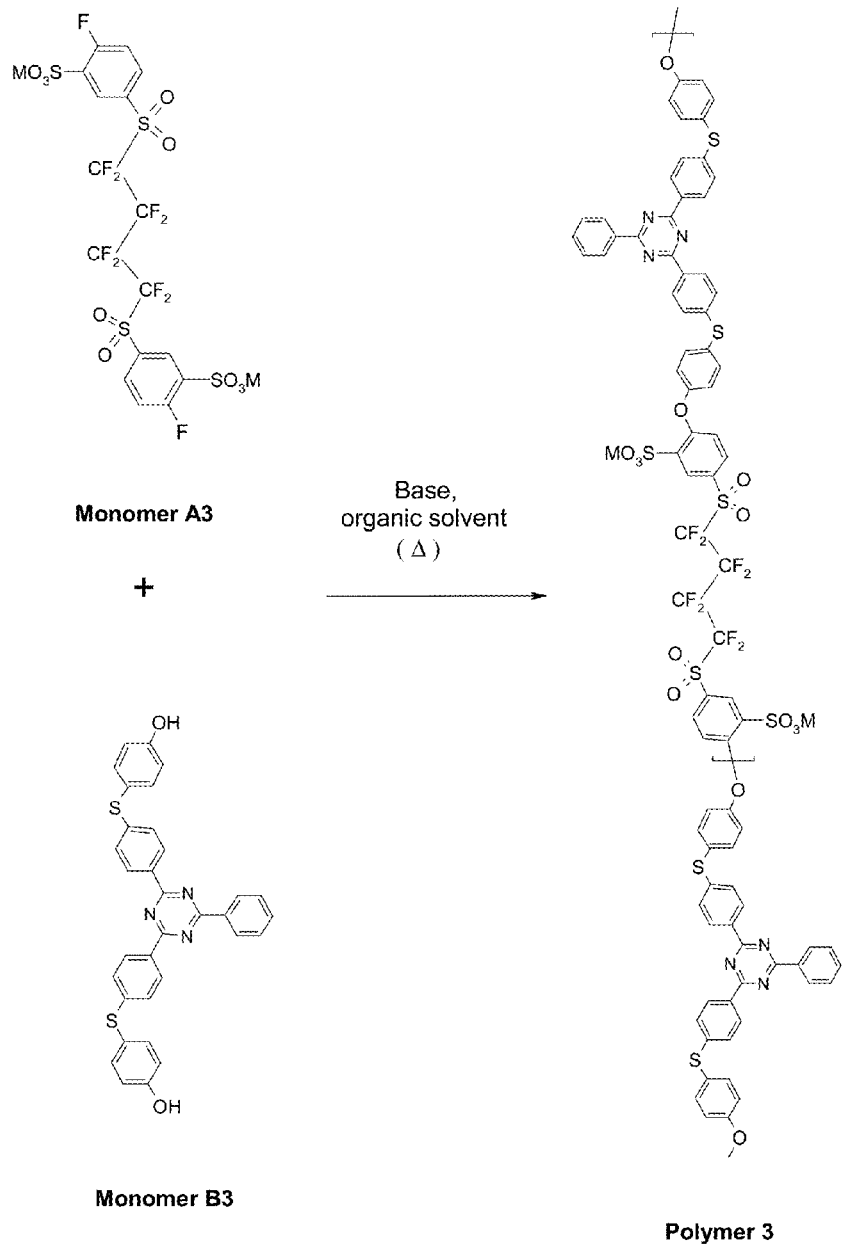
Figure 8:
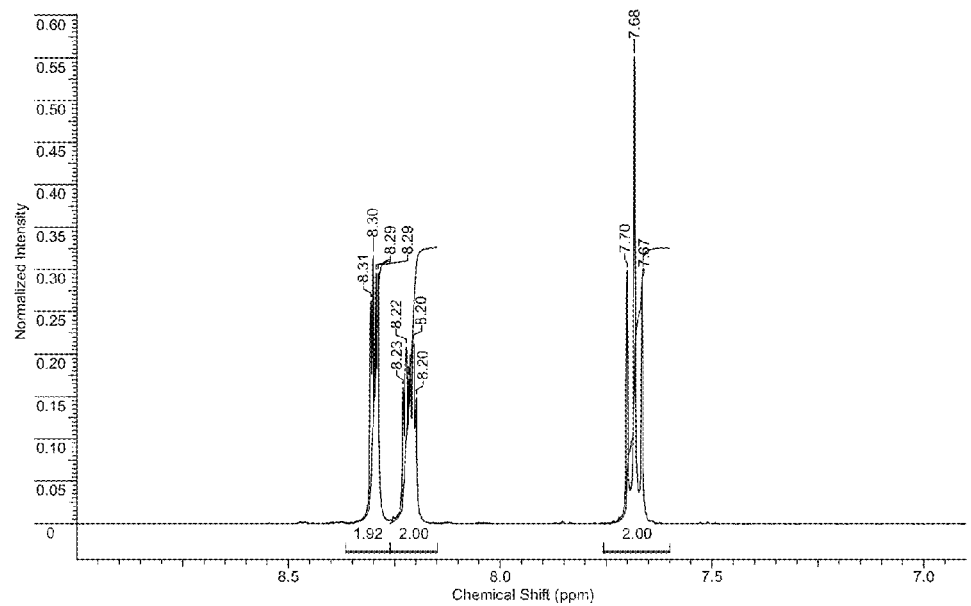
Figure 10:
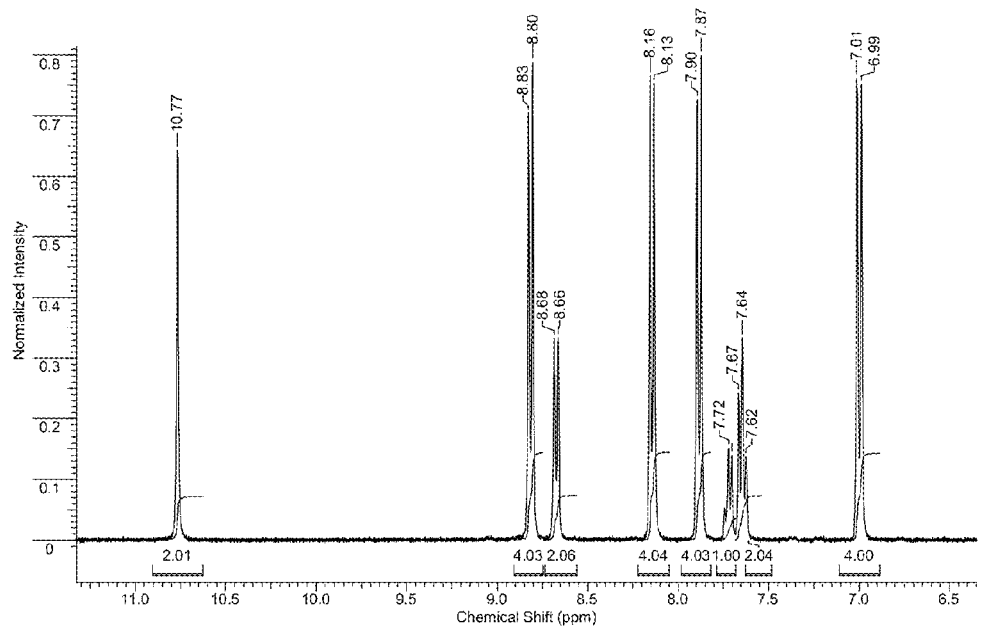
Figure 11:
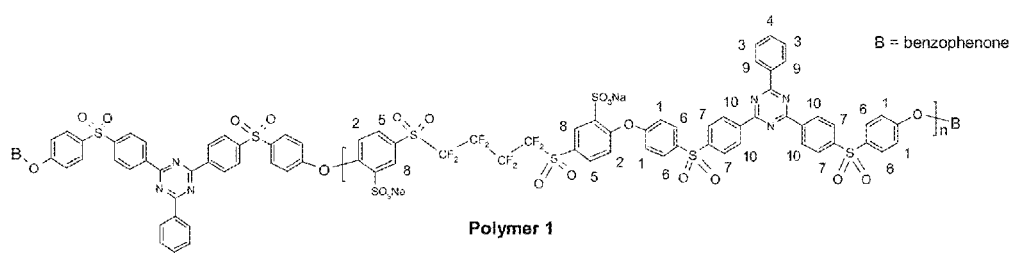
Figure 11:
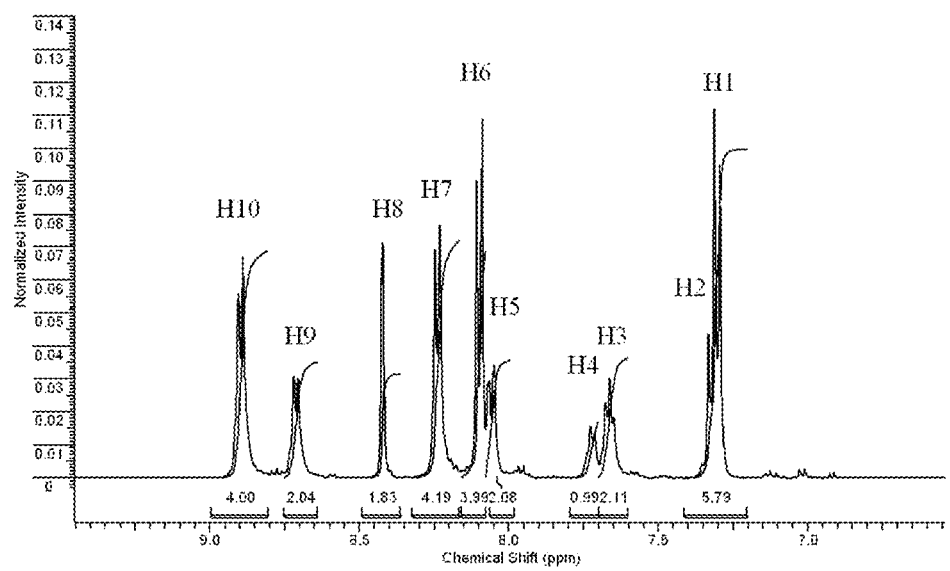
Figure 12:
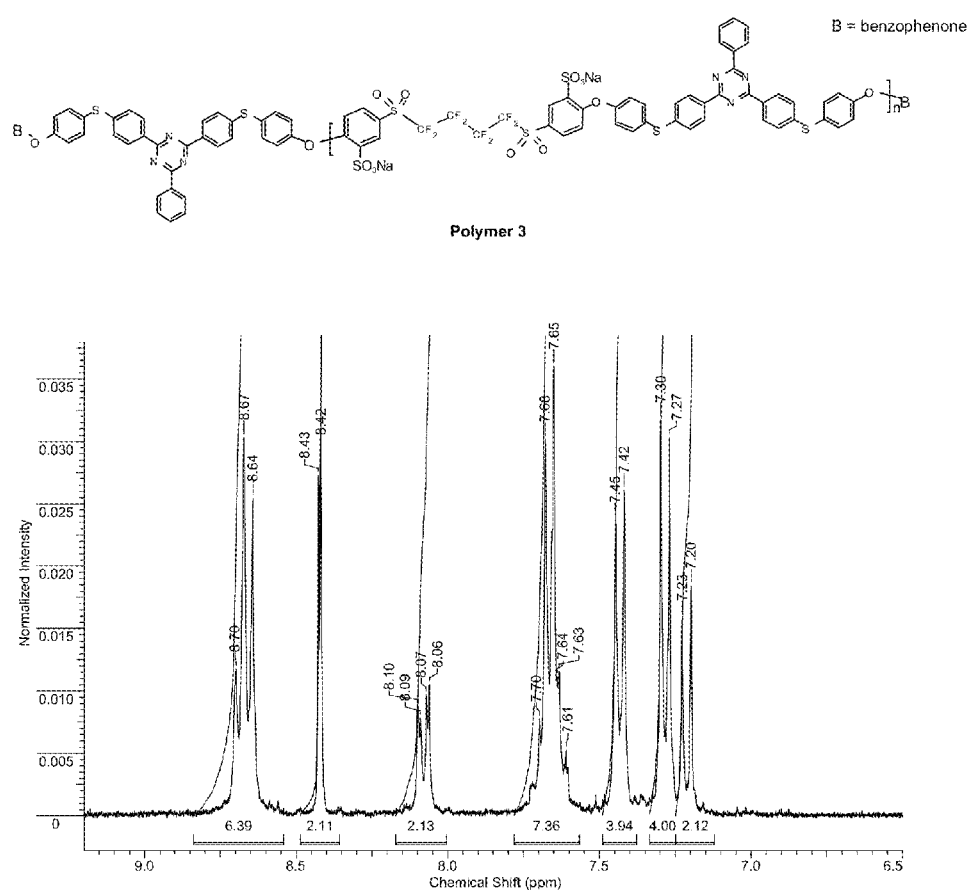
Figure 14:
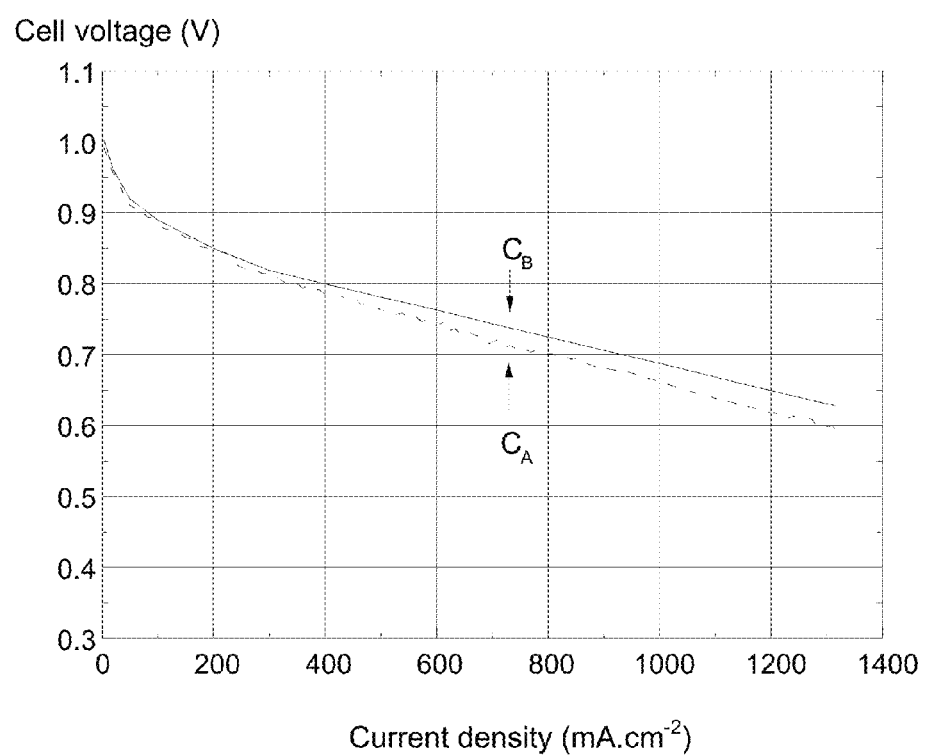

The invention and its advantages will be easily understood in the light of the detailed description and implementational examples which follow, and also of the figures relating to these examples, which represent or schematize:

examples of monomers in accordance with the invention of formula (I), of respective general formulae (I-1), (I-2) and (I-3) (FIGS. 1A, 1B and 1C);

examples of monomers in accordance with the invention of formula (I), of respective specific formulae (II-1), (II-2) and (II-3) (FIGS. 2A, 2B and 2C);

examples of monomers in accordance with the invention of formula (I), of respective specific formulae (III-1), (III-2) and (III-3) (FIGS. 3A, 3B and 3C);

an example of a polymer (Polymer 1) and also a possible scheme for the synthesis of this polymer by polycondensation of a monomer A1 in accordance with the invention with a second monomer B1 not in accordance with the invention (FIG. 4);

an example of a polymer (Polymer 2) and also a possible scheme for the synthesis of this polymer by polycondensation of a monomer A2 in accordance with the invention with a second monomer B2 not in accordance with the invention (FIG. 5);

an example of a polymer (Polymer 3) and also a possible scheme for the synthesis of this polymer by polycondensation of a monomer A3 in accordance with the invention with a second monomer B3 not in accordance with the invention (FIG. 6);

a possible scheme for the synthesis, in three successive stages, of the monomer A1 (or Compound 3) in accordance with the invention (FIG. 7);

the $^1H$ NMR spectrum (500 MHz) of the Compound 3 (monomer A1) dissolved in $d_6$-DMSO (FIG. 8);

a possible scheme for the synthesis, in three successive stages, of the monomer B1 (or Compound 6) not in accordance with the invention (FIG. 9);

the $^1H$ NMR spectrum (500 MHz) of the Compound 6 (monomer B1) dissolved in $d_6$-DMSO (FIG. 10);

the formula of Polymer 1 in the sulphonated and benzophenone-blocked form and also its $^1H$ NMR spectrum (500 MHz), dissolved in $d_6$-DMSO (FIG. 11);

the formula of Polymer 3 in the sulphonated and benzophenone-blocked form and also its $^1H$ NMR spectrum (500 MHz), dissolved in $d_6$-DMSO (FIG. 12);

electron microscopy photographs respectively recorded on a horizontal cross section (FIG. 13A) and a transverse cross section (FIG. 13B) of a PEM membrane consisting of the Polymer 1 (FIG. 13);

comparative polarization curves of a PEM fuel cell using the membrane resulting from the Polymer 1 (curve $C_A$) and a commercial membrane (curve $C_B$) (FIG. 14).

IV. DETAILED DESCRIPTION OF THE INVENTION

The aromatic perfluoroalkane monomer of the invention thus has the essential characteristic of corresponding to the formula (I):

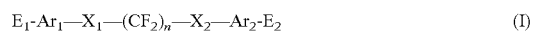

$$E_1-Ar_1-X_1-(CF_2)_n-X_2-Ar_2-E_2 \qquad (I)$$

in which:

n is in a range from 1 to 20;

the symbols $X_1$ and $X_2$, which are identical or different, represent S, SO or $SO_2$;

the symbols $Ar_1$ and $Ar_2$, which are identical or different, represent a phenylene group, at least one of which (that is to say, just one or both phenylene groups) bears a sulphonic group —$SO_3H$ or a sulphonate group —$SO_3M$, M representing an alkali metal cation;

the symbols $E_1$ and $E_2$, which are identical or different, represent an electrophilic functional group.

The term "bearing phenylene group" should be understood as meaning, in the present patent application, that the phenylene group itself or one of the optional replacements for its hydrogen atoms bears a sulphonic or sulphonate group.

In other words, the functionalized perfluoroalkane monomer of the invention of formula (I) thus has the expanded formula:

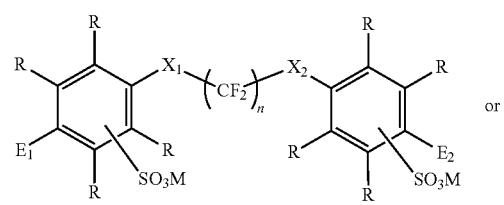

or

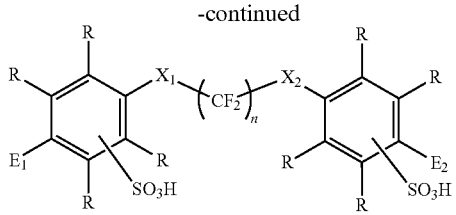

in which R represents hydrogen or a replacement for the hydrogen.

In other words, in the preferred case where $X_1$ and $X_2$ are identical and where just one sulphonate group is present on each phenylene group, the monomer of the invention of formula (I) corresponds, for example, to one of the three formulae I-1, I-2 and I-3 respectively represented in the appended FIGS. 1A, 1B and 1C.

In the above formula (I) and all the preferred alternative forms of the invention described in the present patent application, n preferably varies from 2 to 20, more preferably from 2 to 8; more particularly still, the perfluoroalkane monomer of the invention is a perfluorobutane monomer, that is to say that n is equal to 4.

An essential feature of the monomer of the invention is that at least one of the phenylene groups bears a sulphonic group —$SO_3H$ or a sulphonate group —$SO_3M$, M representing an alkali metal cation, preferably $Na^+$ or $K^+$.

The phenylene groups $Ar_1$ and $Ar_2$ may or may not be substituted by optional substituents other than the sulphonic or sulphonate groups, on the one hand, and other than the electrophilic groups $E_1$ and $E_2$, on the other hand. When such is the case, the invention applies in particular to the cases where just one phenylene group per monomer of formula (I) is substituted and to the cases where several phenylene groups per monomer are substituted, it being possible for just one substituent or several substituents, which are identical or different, to be present on the or the same phenylene group(s).

Mention may in particular be made, as examples of possible optional substituents of the aromatic nuclei (that is to say, more precisely possible optional replacements of the hydrogen atoms of these phenylene groups), of the following substituents:
- —F; —Cl; —Br; —CN; —$CF_3$; —$NO_2$; —$N(CH_3)_2$; —COOH; —COOM; —$PO_3H$; —$PO_3M$; —$SO_3H$; —$SO_3M$ (the symbol M representing an alkali metal cation, preferably $Na^+$ or $K^+$);
- hydroxyl, alkyl, cycloalkyl, perfluoroalkyl, sulphoalkyl, sulphoaryl, aryl, alkylcarbonyl, arylcarbonyl, alkoxyl or aryloxyl radicals.

These optional substituents are preferably selected from the group consisting of the substituents —F, —CN, —$CF_3$, —$PO_3H$, —$PO_3M$ and the mixtures of these substituents.

In the specific case where R is hydrogen, that is to say where none of the phenylene groups is substituted by an optional substituent, then the aromatic perfluoroalkane monomer of the invention corresponds to one of the formulae (I) as represented in the appended FIGS. 1A, 1B and 1C.

The electrophilic functional groups, which confer its polymerizable nature on the monomer of the invention, are well known to a person skilled in the art: to remind, an electrophilic functional group or group (atom or group of atoms) (Lewis acid or electron acceptor) has a missing pair of electrons and is thus capable of creating a covalent bond with a Lewis base; conversely, a nucleophilic functional group or group (atom or group of atoms) (Lewis base or electron donor) has a free pair of electrons and is thus capable of creating a covalent bond with a Lewis acid.

Preferably, $E_1$ and $E_2$, which are identical or different, are chosen from the group consisting of halogens (in particular F, Cl, Br and I), carboxyl (COOH), acyl chloride (CO—Cl), sulphonyl chloride ($SO_2$—Cl), sulphonyl fluoride ($SO_2$—F), isocyanate (NCO) and mixtures of such functional groups or groups.

More preferably still, $E_1$ and $E_2$, which are identical or different, are halogens, in particular fluorine, chlorine and bromine, more particularly still fluorine and chlorine.

Thus, according to a first particularly preferred embodiment, the $E_1$ and $E_2$ groups correspond to the halogen fluorine in the formula (I).

Thus, in the particularly preferred case where the central perfluoroalkylene block is a perfluorobutylene, the aromatic perfluoroalkane monomer of the invention is an alkali metal salt of 3,3'-bis(4-fluorophenylthio)perfluorobutane disulphonate, of 3,3'-bis(4-fluoro-phenylsulphoxy)perfluorobutane disulphonate, or of 3,3'-bis(4-fluorophenylsulphonyl)perfluorobutane disulphonate, respectively corresponding to the formulae (II-1), (II-2) and (II-3) represented in the appended FIGS. 2A, 2B and 2C, in which at least one (that is to say, just one or both) of the two phenylene groups ($Ar_1$ and $Ar_2$) comprises a sulphonic or sulphonate group, these phenylene groups in addition being or not being able to comprise optional substituents, such as those described above.

According to a second particularly preferred embodiment, the $E_1$ and $E_2$ groups correspond to the halogen chlorine in the formula (I). Thus, in the more preferred specific case where the central perfluoroalkylene block is a perfluorobutylene, aromatic perfluoroalkane monomer of the invention of formula (I) is thus an alkali metal salt of 3,3'-bis(4-chlorophenylthio)perfluorobutane disulphonate, of 3,3'-bis(4-chlorophenylsulphoxy)perfluorobutane disulphonate or of 3,3'-bis(4-chlorophenylsulphonyl)perfluorobutane disulphonate, respectively corresponding to the formulae (III-1), (III-2) and (III-3) represented in the appended FIGS. 3A, 3B and 3C, in which at least one (that is to say, just one or both) of the two phenylene groups ($Ar_1$ and $Ar_2$) comprises a sulphonic or sulphonate group, these phenylene groups in addition being or not being able to comprise optional substituents, such as those described above.

The aromatic perfluoroalkane monomer in accordance with the invention described above can advantageously be used for the synthesis of polymers which can constitute, in the sulphonated form, an electrolyte (or membrane, which is equivalent) in a fuel cell. The term "polymer" should be understood as meaning any homopolymer or copolymer, in particular block copolymer, comprising at least structural components resulting from the monomer of the invention.

The term "sulphonated monomer" or "sulphonated polymer" is understood to mean, by definition and in a well known way, a monomer or polymer bearing one or more sulphonic (—$SO_3H$) or sulphonate (—$SO_3M$) groups or mixtures of such groups, M representing a cation of an alkali metal preferably chosen from lithium (Li), caesium (Cs), sodium (Na) and potassium (K), more preferably from sodium (Na) and potassium (K). It will be restated briefly here that it is the sulphonic groups which, in a PEM cell, provide the proton conductivity of the polymer used as membrane.

The appended FIG. 4 represents an example of a polymer which can be synthesized from an aromatic perfluoroalkane monomer in accordance with the invention and also a possible scheme for the synthesis of this polymer from such a monomer.

The polymer (hereinafter referred to as "Polymer 1") as represented in FIG. 4, in the sulphonated form, is composed of two types of structural units connected to one another via ether (—O—) bridges. This Polymer 1 can be prepared by polycondensation of a monomer in accordance with the invention, denoted A1 (in this instance, in the disulphonated form) with a second monomer (monomer of the triazine type) not in accordance with the invention, denoted B1 in FIG. 4, in the presence of a base and of an organic solvent, according to a procedure which will be described in detail later. The monomer A1 corresponds to the aromatic perfluoroalkane monomer of formula (II-3) described above (FIG. 2C).

Another example of a polymer which can be synthesized from an aromatic perfluoroalkane monomer in accordance with the invention and also a possible scheme for the synthesis of this polymer from such a monomer are represented in the appended FIG. 5.

The polymer (hereinafter referred to as "Polymer 2") as represented in FIG. 5, in the sulphonated form, is composed of two types of structural units connected to one another via ether (—O—) bridges. This Polymer 2 can be prepared by polycondensation of a monomer in accordance with the invention, denoted A2 (in this instance, in the disulphonated form), with a second monomer (monomer of the triazine type, also sulphonated) not in accordance with the invention, denoted B2 in FIG. 5, in the presence of a base and of an organic solvent. It should be noted that the monomer denoted in this instance A2 (in order to standardize the references in the different figures) in fact corresponds to the preceding monomer A1 (FIG. 4).

Another example of a polymer which can be synthesized from an aromatic perfluoroalkane monomer in accordance with the invention and also a possible scheme for the synthesis of this polymer from such a monomer are represented in the appended FIG. 6.

The polymer (hereinafter referred to as "Polymer 3") as represented in FIG. 6, in the sulphonated form, is composed of two types of structural units connected to one another via ether (—O—) bridges. This Polymer 3 can be prepared by polycondensation of a monomer in accordance with the invention, denoted A3 (in this instance, in the disulphonated form), with a second monomer (monomer of the triazine type) not in accordance with the invention, denoted B3 in FIG. 6, in the presence of a base and of an organic solvent, according to a procedure which will be described in detail later. It should be noted that the monomer denoted in this instance A3 (to standardize the references in the different figures) also corresponds to the preceding monomers A1 and A2 (FIG. 4 and FIG. 5).

V. EXAMPLES OF THE IMPLEMENTATION OF THE INVENTION

The tests which follow first of all describe in detail the synthesis of the monomers A1 (in accordance with the invention) and B1 (not in accordance with the invention), and then that of the Polymer 1 and Polymer 3.

Subsequently, the Polymer 1 is characterized and tested as a proton-conducting membrane in a fuel cell of the PEM type. In this instance, the Polymer 1 comprises chain ends blocked by benzophenone blocking groups (denoted B in FIG. 11), which are hydrophobic and sterically hindered and which are intended to reduce the solubility of the polymer in water.

In the present description, unless expressly indicated otherwise, all the percentages (%) shown are % by weight.

V-1. Synthesis of the Monomer A1

The monomer A1 is disulphonated 3,3'-bis(4-fluorophenylsulphonyl)perfluorobutane, the formula of which (reproduced in FIGS. 4 and 7, for example) is as follows:

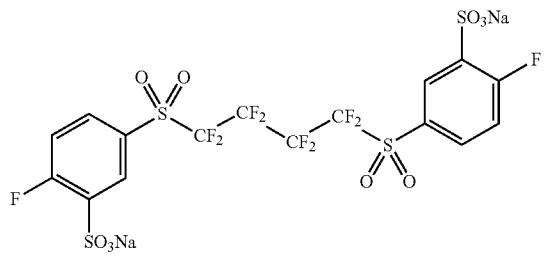

This monomer A1 (or Compound 3 in FIG. 7) was prepared according to the procedure represented diagrammatically in FIG. 7, in three successive stages, as described in detail below.

V-1-A) Stage 1

During a first stage, the Compound 1 or 1,4-bis(4-fluorophenylthio)perfluorobutane is prepared according to the procedure which follows and which is represented diagrammatically in FIG. 7A.

This procedure, although different, is inspired by the process for the synthesis of fluorinated polyethersulphones, as described in the publication by Feiring A. E., Wonchoba E. R. & Arthur R. D., "*Fluorinated Poly(Ether Sulfone)s*", J. Polym. Sci., Part A: Pol. Chem., 1990, 38, 2809-2818.

A mixture of sodium methoxide (13.64 g) (Fluka, 97%) and 4-fluorothiophenol (31.70 g) (Fluorochem, 99%) in 200 ml of anhydrous methanol is heated at reflux for 60 min. After distilling off the methanol, the white solid is kept under nitrogen in the apparatus at ambient temperature.

51.0 g of 1,4-diiodoperfluorobutane (0.110 mol) (Apollo Scientific, 98%) are added to a solution of 37.0 g of sodium 4-fluorophenylthiolate salt (244.83 mmol) in 170 ml of anhydrous DMF, under nitrogen and cooled to 0° C.; an exothermicity occurs and the temperature reaches 40° C. The solution obtained is kept at 40° C. and stirred for approximately 12 hours; it is subsequently heated at 60° C. for 1 hour. The solution, once it has returned to ambient temperature, is diluted with 60 ml of water and then concentrated using a vacuum pump in order to remove 100 ml of solvent. The remaining solution is diluted with water and the lower phase is separated and washed with water. The product is distilled at 120° C. under vacuum. After having removed the impurities, a colourless liquid is recovered, i.e., 37.9 g (75.6%). The remaining traces of impurities (thiol) are removed by column chromatography using hexane as mobile phase, giving a product resembling solid and transparent wax at ambient temperature. The melting point of the product is equal to approximately 50° C. (measured by DSC).

The Compound 1, of formula:

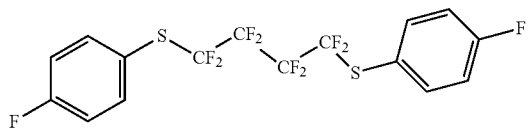 [SMILES: Fc1ccc(SC(F)(F)C(F)(F)C(F)(F)C(F)(F)Sc2ccc(F)cc2)cc1]

is thus obtained.

The NMR analysis gives the following results:
$^1$H NMR, 500 MHz (CDCl$_3$): 7.09-7.12 (m, 4H), 7.62-7.65 (m, 4H).

V-1-B) Stage 2

Then, during a second stage, the Compound 2 or 1,4-bis(4-fluoro-phenylsulphonyl)perfluorobutane is prepared according to the procedure which follows and which is represented diagrammatically in FIG. 7B.

A one liter two-necked round-bottomed flask, equipped with a reflux condenser, a magnetic bar and a nitrogen inlet, is charged with 31.80 g (80.0 mmol) of Compound 4, 350 ml of glacial acetic acid and 65.4 g (i.e., 413 mmol) of $KMnO_4$ (5.9 eq.). After stirring at ambient temperature for 10 min, the solution is cooled to between 0° C. and 5° C. and then 35 ml of concentrated sulphuric acid are added dropwise during the cooling with the ice bath (temperature of between 0 and 5° C., for 5 hours). The reaction mixture is stirred overnight at ambient temperature and is then poured into 3.5 liters of distilled water. The product is extracted with 7 liters of chloroform. The hydrolysed $MnO_2$ is filtered each time through a filter paper plus a textile filter. The solvent (chloroform/acetic acid) is removed using a rotary evaporator at 50° C. The product is then dissolved in 1 liter of chloroform. The organic phase is subsequently successively washed with 200 ml of a saturated $NaHCO_3$ solution and then with 200 ml of distilled water, and is finally dried with $MgSO_4$. The solvent is removed on a rotary evaporator and then the product is purified by column chromatography using a hexane/ethyl acetate/methanol (15/3/2) mixture as eluent, in order to obtain the Compound 2.

The product, in the form of white crystals, is dried overnight at 60° C. under vacuum. It is subsequently recrystallized from acetone in order to obtain transparent crystals. The DSC analysis reveals a melting point of approximately 127° C.

32.6 g (yield 90%) of Compound 2, of formula:

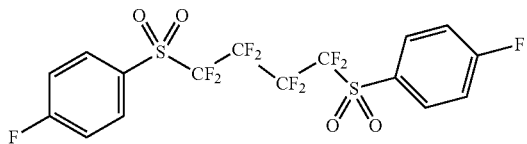 [SMILES: O=S(=O)(c1ccc(F)cc1)C(F)(F)C(F)(F)C(F)(F)C(F)(F)S(=O)(=O)c1ccc(F)cc1]

are thus obtained.

The NMR analysis gives the following results:

$^1$H NMR, 500 MHz ($CDCl_3$): 7.36-7.39 (m, 4H), 8.07-8.10 (m, 4H).

V-1-C) Stage 3

Finally, during a third and final stage, the Compound 3 or monomer A1 (disulphonated 3,3'-bis(4-fluorophenylsulphonyl)perfluorobutane) is prepared according to the procedure which follows and which is represented diagrammatically in FIG. 7C.

The Compound 2 (5.0 g, i.e. 9.65 mmol) is placed in a four-necked round-bottomed flask dried with a hot-air gun and then placed under nitrogen (glass-covered magnetic bar). The concentrated sulphuric acid (23.6 g) is subsequently added using a predried graduated glass cylinder. Most of the compound does not dissolve in the sulphuric acid at ambient temperature (the solution becomes slightly purple). Finally, 20.06 g of oleum (Merck product comprising 65% $SO_3$) are added using a predried graduated dropping funnel. The gas outlet bubbler is filled with concentrated sulphuric acid and the gaseous products are purged through an empty trap and then through a trap filled with 10% NaOH. The reaction medium is heated at 120° C. (temperature of the oil bath of 128° C.) with a moderate stream of nitrogen moving above the solution. The reaction is continued at 120° C. overnight (approximately 12 h).

Once the sulphonation is complete, the reaction mixture is cooled to 90° C. and then poured, still hot, into 250 g of ice. The combined mixture is left stirring; once all the ice has melted, 15 of NaCl are added, precipitating the disulphonated monomer. The precipitate is subsequently filtered off and then dried at 80° C. under vacuum. The dry product is subsequently mixed with 250 ml of distilled water and heated up to 90° C. Once all the product has dissolved, the pH is adjusted to 7.0 by adding 1% NaOH (aqueous). The solution is cooled to ambient temperature; the majority of the product has precipitated at that time. The white product is separated from the aqueous phase by filtration. The product remaining in the aqueous phase is precipitated by adding 15 g of NaCl. The product is filtered off and dried overnight at 150° C. under vacuum. No other purification is necessary.

5.92 g (yield 85%) of monomer A1 in accordance with the invention, of formula:

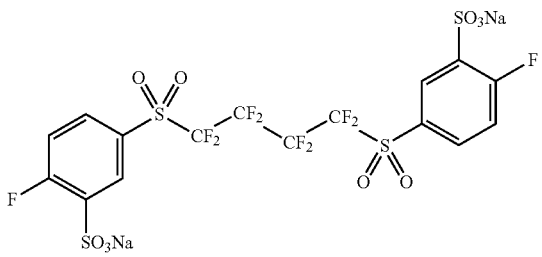

are thus obtained.

The $^1$H NMR spectrum (500 MHz) of the monomer A1 thus obtained, dissolved in $d_6$-DMSO, is reproduced in FIG. 8.

The NMR analysis gives the following results:

$^1$H NMR, 500 MHz ($d_6$-DMSO): 7.67-7.70 (m, 2H), 8.20-8.23 (m, 2H), 8.29-8.31 (m, 2H).

The product appears pure according to a thin layer chromatography ("TLC") analysis on silica plates using a dichloromethane/ethyl acetate/methanol (7:7:6) mixture.

Finally, the molecular weight of the product, as measured by "ESI" (Electrospray Ionization) mass spectrometry (negative mode ($M^-$—$Na^+$); water/acetone 1/1 mixture) is equal to 698.8 (calculated theoretical value equal to 699.5).

V-2. Synthesis of the Monomer B1

The monomer B1, to recapitulate, not in accordance with the present invention, is 2,4-[4-(4-hydroxyphenylsulphonyl)phenyl]-6-phenyl-1,3,5-triazine, the formula of which (already reproduced in FIG. 4) is as follows:

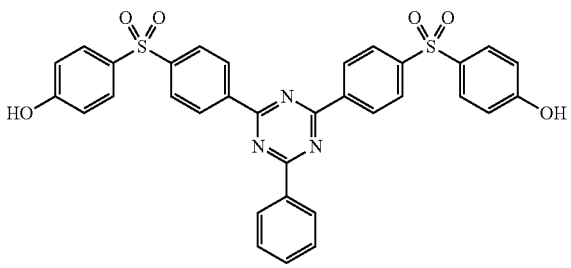 [SMILES: O=S(=O)(c1ccc(O)cc1)c1ccc(-c2nc(-c3ccccc3)nc(-c3ccc(S(=O)(=O)c4ccc(O)cc4)cc3)n2)cc1]

This monomer B1 (or Compound 6 in FIG. 9) was prepared according to the procedure represented diagrammatically in FIG. 9, in three successive stages, as described in detail below.

V-2-A) Stage 1

During a first stage, the Compound 4 or 2,4-bis(p-fluorophenyl)-6-phenyl-1,3,5-triazine is prepared according to the procedure which follows and which is represented diagrammatically in FIG. 9A.

This procedure, although different, is inspired by the process for the synthesis of chlorinated triphenyltriazines as described in the publication by Spencer R. D. & Beggs B. H, "*Determination of Four Closely Related Triaryl-s-Triazines by Infrared Spectroscopy*", Anal. Chem., 1963, 31(11), 1633-1636.

A 500 ml three-necked round-bottomed flask, equipped with a magnetic bar, a reflux condenser and a thermometer, is dried using a hot-air gun (the apparatus is placed under vacuum). 67.8 g of p-fluorobenzonitrile (0.56 mol) (Fluorochem 99%), 36.0 g of ammonium chloride (0.68 mol), 34.0 g of aluminium chloride (0.26 mol) and 32.0 g of benzoyl chloride (0.22 mol) are placed in the round-bottomed flask under nitrogen. The round-bottomed flask is immersed in an oil bath heated to 158° C. and is left overnight at 150° C. (temperature inside the reaction round-bottomed flask), a gentle stream of nitrogen placed above the reaction mixture.

The reaction product is cooled to ambient temperature (approximately 23° C.) and hydrolysed by adding 300 g of ice and 60 g of 36% HCl. The solid is filtered off, then dispersed in water and washed until a neutral pH is obtained. The white solid is stirred in 500 ml of methanol heated at reflux for 30 min and then the mixture is allowed to cool to ambient temperature. To finish, the product is filtered off and dried at 60° C. under vacuum.

26.6 g (yield 35%) of Compound 4 are thus obtained, which product exhibits a melting point (according to DSC) of 254.5° C.

The NMR analysis gives the following results:

$^1$H NMR, 500 MHz ($CD_2Cl_2$): 7.30-7.34 (m, 4H), 7.62-7.65 (m, 2H), 7.68-7.70 (m, 1H), 8.79-8.80 (d, 2H), 8.82-8.85 (m, 4H).

V-2-B) Stage 2

During a second stage, the Compound 5 or 2,4-[4-(4-hydroxyphenylsulphanyl)phenyl]-6-phenyl-1,3,5-triazine is prepared according to the procedure which follows and which is represented diagrammatically in FIG. 9B.

4-Hydroxythiophenol (or 4-HTP) (99%, Acros) is stored under nitrogen and in solid form. The Compound 4 and $K_2CO_3$ are dried separately overnight at 150° C. under vacuum. A magnetic bar is placed in a 2 l round-bottomed flask (equipped with a reflux condenser, a thermometer and a nitrogen inlet/outlet). The apparatus is placed under vacuum and dried. A two-way valve is used to replace the vacuum with nitrogen and to continually purge with the inert gas during the addition of the reactants.

The Compound 4 (9.13 g, i.e., 26.44 mmol) and powdered anhydrous $K_2CO_3$ (9.69 g, i.e., 1.2 eq. with respect to the 4-HTP) are added, while still hot (at the end of drying), to the apparatus purged with nitrogen. This is followed by the addition of 750 ml of anhydrous DMSO. The suspension obtained is subsequently purged for at least 15 min with a stream of nitrogen inside the solution.

The required amount of 4-HTP (7.45 g or 58.42 mmol, i.e., 2.2 eq.), in the liquid form, is transferred using a 10 ml plastic syringe, weighed directly inside the syringe and injected into the reaction mixture. Once all the reactants are added, the nitrogen is purged continuously above the solution. The mixture is heated at 100° C. overnight (20 hours) with continuous stirring and is then allowed to cool to ambient temperature.

The product cannot be purified in a single stage: approximately 250 ml of aliquot fraction of the reaction mixture are withdrawn and poured into a separation funnel (3 liters) containing 2.6 liters of ethyl acetate/water (ratio by weight 1/1). The remainder of the product is kept under a continual stream of nitrogen. The mixture placed in the separation funnel is shaken (the colour changes from orange to lemon yellow) and the desired product is extracted into the ethylene acetate phase (the DMSO/$H_2O$ phase comprises only traces of the desired product). The organic phase is washed with 100 ml of an $NaHCO_3$ solution, which stage is followed by washing with 100 ml of $H_2O$; the organic phase is subsequently dried with anhydrous $MgSO_4$. The process is repeated twice with the other two remaining 250 ml aliquots of the reaction mixture.

The ethyl acetate phase is evaporated using a rotary evaporator; a viscous slightly orange liquid, like honey, remains (comprising a small amount of DMSO). The residual DMSO is removed at 100° C. under reduced pressure. A small amount of acetone (10 ml) is added, followed by 40 ml of diethyl ether. The solid immediately becomes cream white and is filtered off on a ceramic filter. The residual thiol is removed from the reaction product by column chromatography using hexane/$CH_2Cl_2$/ethyl acetate/methanol (ratios by weight 4/2/1/1) as mobile phase.

13.1 g (i.e., a yield of approximately 89%) of the Compound 5 are thus obtained.

The NMR analysis gives the following results:

$^1$H NMR (500 MHz) $d_6$-DMSO: 6.93-6.95 (d, 4H), 7.17-7.19 (d, 4H), 7.42-7.44 (d, 4H), 7.58-7.60 (m, 2H), 7.65-7.68 (m, 1H), 8.49-8.50 (d, 4H), 8.61-8.63 (d, 2H), 10.04 (s, 2H).

The molecular weight of the product, as measured by "MALDI" (Matrix-assisted Laser Desorption/Ionization) mass spectrometry (positive mode; dithranol matrix), is equal to 558.1 (calculated theoretical value equal to 557.7).

V-2-C) Stage 3

Finally, during a third and final stage, the Compound 6 is prepared according to the procedure which follows and which is represented diagrammatically in FIG. 9C.

A 250 ml three-necked round-bottomed flask is equipped with a magnetic bar, a thermometer, a reflux condenser and an opening used for the addition of the reactants. A suspension is prepared by adding 6.69 g of Compound 5 (12 mmol) to 150 ml of glacial acetic acid. Once the reactant has been added, the suspension is heated to 70° C. The reactant dissolves, giving a slight transparent yellow coloration. Subsequently, 18.0 g of 50% hydrogen peroxide (264 mmol) are introduced dropwise into the reaction (no exothermicity is observed). The solution is heated at reflux (100° C.) for 1 hour (slightly yellow coloration). Thin layer chromatography (silica plate) in $CH_2Cl_2$/ethyl acetate/methanol (ratios by weight 3/1/1) makes it possible to monitor the consumption of the reactant during the reaction (the blue fluorescence of the triazine at 325 nm disappears with the oxidation).

Subsequently, 50 ml of acetic acid are removed by distillation at reduced pressure (vacuum generated by a water pump). After distillation, during the cooling, white crystals begin to precipitate from the solution as soon as the temperature falls below 80° C. The solution is left overnight at ambient temperature in order for the product to crystallize from the acetic acid. The acetic acid is then removed by filtration and the final white product is washed with 300 ml of distilled water. Subsequently, approximately 18 g of wet product thus obtained are transferred into a round-bottomed flask and 75 ml of distilled water are added, the combined mixture being stirred for approximately 15 min. The product is subsequently filtered off and washed up to a value of neutral pH. The product, which is still wet, is dried at 60° C. under vacuum for 2 h and then at 100° C. under vacuum overnight (approximately 12 h).

Purification is carried out by column chromatography using CH$_2$Cl$_2$/ethyl acetate/methanol (3/1/1) as mobile phase.

The endothermic peak lies at approximately 294° C. (1$^{st}$ DSC run). It is recorded that the monomer immediately polymerizes during the second DSC run; the glass transition temperature (Tg) of the polymer thus formed lies at approximately 145° C.

5.35 g (yield of approximately 80%) of the Compound 6 or monomer B1 are thus obtained.

The $^1$H NMR spectrum (360 MHz) of the monomer B1 thus obtained, dissolved in d$_6$-DMSO, is reproduced in FIG. 10.

The NMR analysis gives the following results:
$^1$H NMR (360 MHz) d$_6$-DMSO: 6.99-7.01 (d, 4H), 7.62-7.67 (m, 2H), 7.72 (t, 1H), 7.87-7.90 (d, 4H), 8.13-8.16 (d, 4H), 8.66-8.68 (d, 2H), 8.80-8.83 (d, 4H), 10.77 (s, 2H).

Finally, the molecular weight of the product, as measured by "ESI" (Electrospray Ionization) mass spectrometry (negative mode; water/acetone 1/1 mixture), is equal to 620.7 (calculated theoretical value equal to 621.7).

V-3. Synthesis of the Polymer 1

This example describes, in a detailed manner, the synthesis, from the monomers A1 in accordance with the invention and B1 not in accordance with the invention described above, of the Polymer 1 in the sulphonated form, blocked by benzophenone groups, as represented in FIG. 11.

The monomer B1 is dried at 60° C. under vacuum overnight. The monomer A1 and Na$_2$CO$_3$ are dried separately at 150° C. under vacuum overnight. The three compounds are then mixed and dried at 160° C. under vacuum for one hour. The copolymerization of monomers A1 and B1 takes place in a 100 ml three-necked round-bottomed flask. The round-bottomed flask is equipped with a nitrogen inlet, a thermometer, a magnetic stirrer and a Dean & Stark separator surmounted by a reflux condenser. The glass parts of the apparatus are dried under vacuum using a hot-air gun in order to reach a temperature of at least 100° C. in the round-bottomed reaction flask.

The round-bottomed reaction flask is charged with the monomer B1 (1.89 g, i.e., 3.04 mmol or 1 eq.), the monomer A1 (2.20 g, i.e., 3.04 mmol or 1 eq.), the anhydrous sodium carbonate (0.97 g, i.e., 9.13 mmol or 3 eq.), anhydrous N,N-dimethylacetamide (20 ml) and toluene (4.0 ml, azeotropic agent). The round-bottomed reaction flask is heated at 100° C. in an oil bath for one hour (azeotropic distillation). The valve for circulation of the toluene is subsequently closed and the toluene is distilled off at 100° C. The temperature of the oil bath is subsequently increased to approximately 148° C. and the residual toluene is removed by distillation for an additional 60 min, so that all the toluene is removed from the reaction and so that the temperature increases to 140° C. inside the round-bottomed flask. The toluene is emptied from the Dean & Stark separator and the temperature of the oil bath is increased to approximately 159° C. and maintained at this value overnight. After approximately 20 h, the temperature of the oil bath is increased to approximately 168° C. (approximately 152° C. inside the round-bottomed flask) and the polymerization continues for 4 hours. The temperature of the reaction is brought down to approximately 130° C. inside the round-bottomed flask by removing the round-bottomed flask from the oil bath. 8 mg of 4-fluorobenzophenone dissolved in 5 ml of anhydrous N,N-dimethylacetamide are subsequently added to the reaction using a syringe. The round-bottomed flask is placed back in the oil bath and the reaction continues at approximately 152° C. (168° C. in the oil bath) for a period of an additional 4 h. The reaction mixture is allowed to cool to ambient temperature and the polymer is subsequently poured into 500 ml of 2-propanol (isopropanol). The fibrous precipitate is recovered by filtration and washed with isopropanol and with water until a neutral pH is obtained (washing out of the residual salts). The product is subsequently dried at 60° C. under vacuum overnight. Purification is carried out by precipitation of the polymer, dissolved in N,N-dimethylacetamide, poured dropwise into diethyl ether with continual stirring.

The formula of the Polymer 1 thus obtained, in the sulphonated and benzophenone-blocked form, is represented in FIG. 11, along with its $^1$H NMR spectrum (500 MHz), dissolved in d$_6$-DMSO.

V-4. Synthesis of the Polymer 3

This example describes in a detailed way the synthesis of the Polymer 3, according to a process already commented on in FIG. 6, from the monomers A3 (Compound 3) and B3 (Compound 5) described above, this Polymer 3 being obtained here, on the one hand, in the sulphonated form and, on the other hand, in the form blocked by benzophenone groups, as represented in FIG. 12.

The monomer denoted B3 (Compound 5) is dried at 80° C. under vacuum overnight. The monomer denoted A3 (Compound 3) and Na$_2$CO$_3$ are dried separately at 150° C., mixed and then the combined mixture is dried at 160° C. under vacuum for one hour. The copolymerization of the monomers A3 and B3 is carried out in a 100 ml three-necked round-bottomed flask. The round-bottomed flask is equipped with a nitrogen inlet, a thermometer, a magnetic stirrer and a Dean & Stark separator surmounted by a reflux condenser. The glass parts of the apparatus are dried under vacuum.

For a 50 mol % disulphonation, the round-bottomed flask is charged with the monomer B3 (1.695 g, i.e., 3.04 mmol or 1 eq.), the monomer A3 (2.196 g, i.e., 3.04 mmol or 1 eq.), the anhydrous sodium carbonate (0.968 g, 9.13 mmol, 3 eq.), anhydrous N,N-dimethylacetamide (20 ml) and toluene (4.0 ml, azeotropic agent). The round-bottomed reaction flask is heated at 100° C. in an oil bath for two hours (azeotropic distillation). The valve for circulation of the toluene is subsequently closed and the toluene is distilled off at 100° C. The temperature of the oil bath is subsequently increased to 148° C. and the residual toluene is removed by distillation for an additional one hour, so that all the toluene is removed from the reaction and so that the temperature reaches 140° C. inside the round-bottomed flask. The toluene is emptied from the Dean & Stark separator and the temperature of the oil bath is increased to 159° C. and then maintained at this value overnight.

After approximately 20 h, the round-bottomed flask is removed from the oil bath and allowed to cool down to approximately 130° C. inside the round-bottomed reaction flask. 8 mg of 4-fluorobenzophenone are then dissolved in 5 ml of anhydrous N,N-dimethylacetamide and the solution is added to the reaction using a syringe. The round-bottomed flask is placed back in the oil bath and the reaction continues at approximately 145° C. (approximately 158° C. in the oil bath) for an additional 4 h. The reaction mixture is allowed to cool to ambient temperature; the product obtained is subsequently poured into 200 ml of 2-propanol. The fibrous precipitate is recovered by filtration.

The polymer is then dried under vacuum at 80° C. overnight. The sodium carbonate is extracted from the polymer by immersing the latter in 50 ml of distilled water with stirring with a magnetic bar for 30 min. The pH of the solution is adjusted down to 7 by dropwise addition of 10% HCl (aq.). The polymer is subsequently dried at 80° C. under vacuum (approximately 12 hours).

The formula of the Polymer 3 thus obtained, in the sulphonated and benzophenone-blocked form, is represented in FIG. 12, along with its $^1$H NMR spectrum (500 MHz), dissolved in $d_6$-DMSO.

V-5. Manufacture of PEM Membranes

In this test, Polymer 1 membranes are prepared according to the "solvent casting" technique as described below.

The polymer (625 mg), dissolved beforehand in 8 ml of N,N-dimethylacetamide, is filtered through a PTFE (polytetrafluoroethylene) microfilter ("Millipore") having a pore size of approximately 0.45 μm. The polymer solution thus filtered is then run into a mould consisting of two superimposed glass sheets, the upper sheet comprising a recess (dimensions 9 cm×9 cm) with a depth equal to 1 mm; the solution is subsequently heated at 50° C. for 24 h and then at 60° C. for 2 h. The traces of organic solvent are then removed from the membrane thus formed by immersing the latter in a bath of distilled water for approximately 12 h.

After final drying at 60° C. under vacuum for 2 h, a strong and transparent membrane, with a thickness which is equal to approximately 50 μm, is thus obtained, which is ready for characterization.

V-6. Characterization of the PEM Membranes

V-6-A) Proton Conductivity

For the acidification of the membrane (to remind, exchange of the M$^+$ cation by H$^+$), the Polymer 1 is initially immersed in 200 ml of $H_2SO_4$ (aq.) for 2 h. Use is made of the acid $H_2SO_4$ distilled twice (Sigma Aldrich), in order to avoid traces of metals. Distilled water is subsequently added in several stages (total duration approximately 12 h) in order to reach a pH equal to 7; the membrane is subsequently thus stored in the distilled water overnight (approximately 12 hours).

The proton conductivity of the membrane, expressed in S/cm (Siemens per centimeter) is determined as indicated below.

Membranes in the form of discs with a diameter of 2 cm (thickness 50 μm) are cut out using a hollow punch. The proton conductivity of the membrane is determined by measuring the real part (Ohmic) and the imaginary part (Capacitance) of the complex impedance, within the range of frequencies lying between 100 kHz and 10 Hz (with amplitude of 100 mV AC). The measurements are carried out with an impedance/AC potentiostat (Zahner, Germany). Nyquist graphs are generated by the measurements of a successive stack of one, two, three and up to six membranes (completely humidified) sandwiched between two platinum electrodes having the same circular shape as the membranes.

For each measurement, the value intercepting the real axis of the Nyquist graph is given, that is to say a value of the imaginary component of the impedance at zero. In general, these points are aligned on an affine straight line, the slope of which directly determines the value of the resistance of the membrane. Its ordinate at the origin determines the contact resistance between the membranes and the platinum electrodes. The latter values and the knowledge of the thickness make it possible to calculate in a known way the resistivity of the membrane; the inverse of this value is the conductivity.

Thus tested, the membrane resulting from the Polymer 1 has shown noteworthy proton conductivity values equal to approximately 89 mS/cm, greater than the conductivity value (approximately 70 mS/cm) measured on the commercial membrane ("Nafion® 112") with the same thickness and rigorously tested under the same conditions.

V-6-B) Water Absorption Capacity and Dimensional Stability

Once the membrane has been acidified, it is dried at 100° C. under vacuum for 2 hours. Its weight is immediately measured, before it captures atmospheric moisture. The membrane samples are then immersed in distilled water at ambient temperature until saturated (at this stage, no additional weight gain due to water is then observed).

The water absorption capacity, expressed in %, is calculated as the difference between the weight of the wet membrane and the weight of the dry membrane. The dimensional stability, also expressed in %, is the ratio of the main dimension of the dry membrane to the main dimension of the completely humidified membrane.

It is noted that the membrane of the Polymer 1 has a water absorption capacity equal to 27% of its weight, in comparison with a value of approximately 23% for the commercial membrane ("Nafion® 112"). Its dimensional stability is equal to 20%, in comparison with a value of 7% for the control commercial membrane.

In other words, it is found that the membranes resulting from the monomers in accordance with the invention unexpectedly exhibit a water absorption capacity and a dimensional stability which are similar to those of the control commercial membrane, so many factors which are determining for the endurance and the chemical stability of the membrane while operating in a PEM fuel cell.

V-6-C) Surface Morphology

Horizontal and transverse membrane cross sections are produced (each sample with a thickness of approximately 70 nm) and are then coated in a liquid epoxy resin. The resin is then polymerized at 60° C. for 48 h in the presence of a curing agent and an accelerator.

After impregnating the membrane samples in an aqueous solution of uranyl acetate ($UO^{2+}$ $(CH_3COO^-)_2$) and then of lead citrate, the morphology of the membrane is observed using a transmission electron microscope (Philips TEM CM100; magnification 245 000).

The electron microscopy photographs, respectively recorded on a horizontal cross section (FIG. 13A) and on a transverse cross section (FIG. 13B) of a membrane of the Polymer 1, are reproduced in FIG. 13.

A mean pore size equal to 2.4 nm with a standard deviation of 0.5 nm constitutes a particularly noteworthy and unexpected result for a person skilled in the art. In comparison with the known commercial membranes, the invention thus makes it possible to obtain a greatly improved surface morphology with, on the one hand, very substantially reduced pore sizes and, on the other hand, a particularly narrow distribution in the sizes; such characteristics are determining for the overall electrical performance of the membrane, for its properties of impermeability to gases and for its final endurance.

V-6-D) Performance in a PEM Fuel Cell

The performances of the membranes can be tested on a test bed for fuel cells on which the temperature, the pressure, the flow rate and the humidity of the gases can be regulated. The gases used are pure hydrogen and pure oxygen, at a temperature of 65° C.

The fuel cell used in these tests is composed of a single cell comprising the polymer membrane to be tested, positioned between two "GDE" (Gas-Diffusion Electrode) layers, two graphite bipolar plates and two standard electrodes ("ELE 0107" from Johnson Matthey) having a platinum content of approximately 0.4 mg/cm$^2$.

The membrane to be tested is first of all dried between two nonwovens (sterile chamber grade, "Sontara Micropure 100"—supplier DuPont). It is subsequently pressed between two glass plates at 60° C. for 3 h. The MEA assembly is obtained by hot pressing a Pt/C catalysis layer positioned on each side of the membrane (115° C., 125 MPa). At this stage, the MEA assembly can be assembled between two bipolar plates to form a single cell of a fuel cell which is ready to operate when it is fed with hydrogen and oxygen.

For the requirements of the test, the fuel cell is subjected to stationary conditions (0.7 V) or to shutdown and startup or "OCV" (Open Circuit Voltage) situations, in order, in a known way, to subject the membrane to the most aggressive operating conditions (e.g., peroxides, free radicals, and the like) and to finally deduce therefrom its overall chemical resistance.

FIG. 14 reproduces the "polarization" curve, the voltage of the single cell being recorded as a function of the current density delivered by the fuel cell, on the one hand for the membrane consisting of the Polymer 1 (curve $C_A$) and, on the other hand, for the commercial membrane ("Nafion® 112" polymer, curve $C_B$).

The following comments result from the reading of these two curves:
- first of all, at high voltage and zero current (open electrical circuit), it is noted that the polarization voltage is equivalent for the two membranes, which illustrates, to a person skilled in the art, an equivalent permeability to the gases ($O_2$ and $H_2$);
- subsequently, a substantially identical slope of the two curves is observed in their central linear part (typically between 200 and 1200 mA/cm$^2$), which testifies to an identical electrical performance of the two membranes, without even a particular optimization of the electrodes (anode and cathode) for the specific membrane of the invention;
- finally, at high current and low voltage (typically above 1200 mA/cm$^2$), it is observed that the behaviour of the two membranes remains similar, which confirms a very good proton conductivity of the membrane at high current.

In conclusion, the monomers of the invention make it possible to manufacture polymers and PEM membranes which, unexpectedly, exhibit a chemical and dimensional stability and an ion conductivity which are similar to those of the commercial membranes of the Nafion® type which have, however, been developed for a very long time; in addition, these polymers exhibit an excellent chemical stability and an increased resistance to oxidation.

The invention claimed is:

1. A sulphur-containing and sulphonated aromatic perfluoroalkane monomer corresponding to a formula (I):

$$E_1\text{-}Ar_1\text{—}X_1\text{—}(CF_2)_n\text{—}X_2\text{—}Ar_2\text{-}E_2 \qquad (I)$$

in which:
- n is in a range from 1 to 20;
- $X_1$ and $X_2$, which are identical or different, represent S, SO, or $SO_2$;
- $Ar_1$, $Ar_2$, which are identical or different, represent a phenylene group, at least one of $Ar_1$ and $Ar_2$ bearing a sulphonic (—$SO_3H$) group or a sulphonate (—$SO_3M$) group, in which M represents an alkali metal cation; and
- $E_1$ and $E_2$, which are identical or different, represent an electrophilic functional group.

2. The monomer according to claim 1, wherein n is in a range from 2 to 20.

3. The monomer according to claim 1, wherein n is in a range from 2 to 8.

4. The monomer according to claim 1, wherein $E_1$ and $E_2$, which are identical or different, are chosen from the group consisting of halogen, carboxyl, acyl chloride, sulphonyl chloride, sulphonyl fluoride, isocyanate, and combinations thereof.

5. The monomer according to claim 4, wherein $E_1$ and $E_2$, which are identical or different, represent halogens.

6. The monomer according to claim 5, wherein the monomer corresponds to a formula (II):

$$F\text{—}Ar_1\text{—}X_1\text{—}(CF_2)_n\text{—}X_2\text{—}Ar_2\text{—}F \qquad (II).$$

7. The monomer according to claim 5, wherein the monomer corresponds to a formula (III):

$$Cl\text{—}Ar_1\text{—}X_1\text{—}(CF_2)_n\text{—}X_2\text{—}Ar_2\text{—}Cl \qquad (III).$$

8. The monomer according to claim 1, wherein n is equal to 4.

9. The monomer according to claim 2, wherein n is equal to 4.

10. The monomer according to claim 3, wherein n is equal to 4.

11. The monomer according to claim 4, wherein n is equal to 4.

12. The monomer according to claim 5, wherein n is equal to 4.

13. The monomer according to claim 6, wherein n is equal to 4.

14. The monomer according to claim 7, wherein n is equal to 4.

* * * * *